United States Patent [19]

Lee

[11] Patent Number: 5,501,849
[45] Date of Patent: Mar. 26, 1996

[54] EMOLLIENT COMPOSITION

[75] Inventor: William H. Lee, Romford, United Kingdom

[73] Assignee: Bioglan Ireland (R&D) Limited, Ireland

[21] Appl. No.: 119,240

[22] PCT Filed: Mar. 26, 1992

[86] PCT No.: PCT/GB92/00556

§ 371 Date: Sep. 24, 1993

§ 102(e) Date: Sep. 24, 1993

[87] PCT Pub. No.: WO92/17208

PCT Pub. Date: Oct. 15, 1992

[30] Foreign Application Priority Data

Mar. 26, 1991 [GB] United Kingdom .................. 9106365

[51] Int. Cl.$^6$ ..................................................... A61K 7/42
[52] U.S. Cl. .............................. 424/59; 514/863; 514/873
[58] Field of Search ..................................... 514/873, 863; 424/59

[56] References Cited

U.S. PATENT DOCUMENTS

| 4,194,007 | 3/1980 | Van Scott et al. | 514/863 |
| 4,424,234 | 1/1984 | Olderson et al. | 514/847 |
| 4,608,392 | 8/1986 | Jacquet et al. | 514/725 |
| 4,642,318 | 2/1987 | Wolff | 514/863 |
| 4,678,663 | 7/1987 | Scott et al. | 514/886 |
| 4,696,946 | 9/1987 | Green et al. | 514/863 |
| 4,994,263 | 2/1991 | Lang et al. | 514/887 |

OTHER PUBLICATIONS

Cosmetics & Toiletries, vol. 104, May 1989, Raab, The Use of Tanning Accelerators: "Sense, Nonsense or Danger" 1989.

*Primary Examiner*—Jane Fan
*Attorney, Agent, or Firm*—Wolf, Greenfield & Sacks

[57] ABSTRACT

An emollient composition, for use in a method of treating a psoriasis in which abnormal skin is exposed to actinic or ultraviolet radiation, comprising a lipophilic emollient, wherein the composition is a non-viscous liquid which, on application to skin or a like surface, spreads to provide a substantially uniform coating of the lipophilic emollient, and wherein the coating does not absorb a significant amount of the incident actinic or ultraviolet radiation and is sufficiently non-volatile to persist for a period of sufficient length, for a therapeutically effective dose of incident radiation to be administered.

22 Claims, No Drawings

EMOLLIENT COMPOSITION

DESCRIPTION

This application is a 371 of PCT/GB 92/00556 Mar. 26, 1992.

This invention relates to an emollient for use in a method of treating psoriasis in which the abnormal skin is exposed to Ultraviolet light (UV), preferably to UVA.

Psoriasis has been treated successfully by irradiating effected areas of skin with ultraviolet light, since this method was first proposed by Goeckerman (North West Med, 24: 229–231, 1925). The original Goeckerman regime requires the effected area to be topically treated with crude coal tar, the subsequent removal of the crude coal tar with olive oil, followed by irradiation of the area with ultraviolet light from a medium pressure mercury discharge lamp. In a modern development of this original therapy, known as PUVA treatment, a psoralen, such as trimethylpsoralen, or 8-methoxypsoralen is administered, either systemically or topically to the effected area and the effected area is subsequently irradiated with UVA radiation. The PUVA treatment appears to be a most effective treatment for psoriasis and has been in use since first being described in 1974 (Parrish et.al. New England Journal of Medicine, Vol. 29, No.23, 1974). Also some good results have been achieved by irradiating psoriatic plaques, coated with an emollient, with UVB (See Fischer, Acta Dermatovener (Stockh)56; 473–479, 1976).

In both PUVA and other similar treatments, it has been a common practice to coat the skin with an emollient prior to treatment, in order to ensure that diseased areas of skin receive a sufficient dose of radiation, while preventing the skin from flaking and suffering localised burning. There are numerous air spaces between the abnormal corneocytes in dry psoriatic plaques and, accordingly, if no emollient is used, incident ultraviolet radiation must pass through many air/skin boundries, before impinging upon the epidermis below, where it may have a therapeutic effect. At each air/skin boundry a certain amount of light is reflected and, thus, the many such boundries present in dry psoriatic skin can reflect a significant amount of radiation. The effect of an emollient is to fill these air spaces and to render the scales of skin translucent by decreasing the reflection of incident ultraviolet light. It has been shown that the transmission of ultraviolet light through psoriatic plaques can be increased between 2 and 3 times by the use of an emollient (see Leroy et.al. Photo dermatol 3, 1986, 51–52; J. A. Parrish Phototherapy of Skin diseases and; R. R. Anderson and J. A. Parrish, the Optics of Human Skin, J. Invest. Dermatol. 1981; 77: 13–19.).

In this way, the transmission properties of psoriatic plaques can be rendered similar to that of a normal stratum corneum and the therapeutically effective dose of radiation can be reduced to a level less likely to be harmful (by way of causing painful erythema or burning) to normal skin, which it is often impossible to avoid irradiating when carring out PUVA or like treatments. Thus, an emollient can prevent damage to normal skin, while allowing a therapeutically effective dose of radiation to be given to adjacent diseased areas.

The emollients employed up to date in PUVA therapy and phototherapy using UVB, all absorb a certain amount of ultraviolet light and, thus, reduce the amount of such radiation that reaches the epidermis (this effect is usually outweighed by the previously discussed enhancement of transmission through scaly skin.). In order to overcome this difficulty, patients can be exposed to radiation for longer periods, or to higher intensities of radiation, in order to provide a therapeutic dose of radiation. In theory, this practice should not increase the amount of radiation penetrating skin coated with an emollient.

Where the effected areas of skin are extensive, it is common practice for a sufferer's entire body to be irradiated, in a light cabinet, after an appropriate emollient has been applied to all exposed areas of skin.

A well documented harmful side effect of exposure to ultraviolet light is that, after significant periods of exposure, skin cancers can be developed. For this reason, PUVA treatment and phototherapy with UVB tend to be used on older individuals, whose life expectancy is generally shorter than the period required for most skin cancers to develop at the level of exposure to radiation which their treatment involves. The use of emollients has allowed the exposure to radiation during PUVA treatment to be reduced, without reducing the efficacy of the treatment, and, therefore, has allowed younger patients to enjoy the benefits of the treatment. However, further reductions in the amount of UV exposure required would reduce still further any cancer risk as well as the amount of erythema caused by PUVA treatment.

According to a first aspect of the present invention there is provided an emollient composition, for use in a method of treating psoriasis in which abnormal skin is exposed to incident therapeutic radiation, comprising a lipophilic emollient and an active agent, wherein the active agent is trimethylpsoralen, 8-methoxypsoralen or urocanic acid and the composition is a non-viscous liquid which, on application to skin or a like surface, spreads to provide a substantially uniform coating of the lipophilic emollient and active agent, and wherein the coating does not absorb a significant amount of the incident therapeutic radiation and is sufficiently non-volatile to persist for a period of sufficient length, for a therapeutically effective dose of incident radiation to be administered.

The spreading property of the composition is such that, when applied to skin (either healthy or diseased) the lipophilic emollient and the active agent spread sufficiently thinly and evenly for their distribution to be uniform, in the sense that no areas of skin, covered by the composition, receive a coating of lipophilic emollient and active agent which is significantly heavier or lighter than adjacent such areas. The emollient composition can include a relatively non-volatile lipophilic emollient, which does not absorb a significant amount of the incident therapeutic radiation. Preferably, the incident therapeutic radiation is of a wavelength within the broad band UV, UVA, or UVB regions of the electromagnetic spectrum.

The active agents, employed in this aspect of the invention are effective in stimulating melanocytes to produce melanin. The preferred active agents are 8-methoxypsoralen or trimethylpsoralen, which are preferably included in a concentration of between 0.1% and 10% by weight.

An advantage of the first aspect of the invention is that, by using an emollient composition in accordance with the invention in place of an orally administered melanin production stimulant together with a separate emollient, any systemic side effects of the melanin production stimulants can be avoided. Also, certain disadvantages, associated with known methods for topically administering these substances, are overcome by these embodiments of the invention. For example, it is known to topically apply a psoralen by painting an alcoholic solution thereof onto the areas to be treated. However, this method can result in an uneven coverage of psoralen on the skin, a difficulty not encountered with the present invention, which spreads the psoralen, or the like, out in a uniform coating with the lipophilic emollient. Another known method of topically applying a psoralen is by immersing the body, to be treated, in a bath filled with the psoralen in water. This method does provide a substantially even coverage of psoralen, with the exception of a water level "tide" mark (i.e. around a patient's neck). However it also involves a gross waste of psoralen, since a great deal of the drug is needed to provide a sufficient concentration in the water. Again, neither of these disadvantages are encountered when the psoralen, or the like, is applied in an emollient composition in accordance with the present invention.

In an embodiment, the lipophilic emollient is chosen so that a 5 μm layer thereof absorbs 20% or less and, preferably, 10% or less of the incident therapeutic radiation. Preferably, a 5 μm layer of the lipophilic emollient absorbs 20% or less and, more preferably, 10% or less incident radiation at any wavelength within the broad band UV, UVA or UVB regions of the electromagnetic spectrum.

In embodiments, the composition can comprise a non-volatile and relatively thick lipophilic emollient dissolved in a non-viscous, volatile and non-polar solvent.

In this specification broad band UV is defined as radiation of a wavelength between 285 and 400 nm, UVA has a wavelength of 320–400 nm and UVB a wavelength of 285-320 nm.

According to a second aspect of the invention, there is provided an emollient composition, for use in a method of treating psoriasis in which abnormal skin is exposed to incident broad band UV, UVA or UVB radiation, comprising a lipophilic emollient, wherein the composition is anhydrous, has a viscosity of between 5 and 2500 centipoise and, on application to skin or a like surface, spreads to provide a substantially uniform coating of the lipophilic emollient which, when spread in a 5 μm layer, absorbs 10% or less of the incident therapeutic radiation, has a partial vapour pressure of 10 mmHg or less, at 20° C., and is sufficiently non-volatile to persist for a period of sufficient length, for a therapeutically effective dose of incident radiation to be administered.

When an emollient in accordance with the present invention is employed in a PUVA or like treatment, the amount of ultraviolet radiation required to have a therapeutic effect on scaley skin is reduced, in much the same way as it is when conventional emollients are employed. Thus the radiation dose received by adjacent normal skin, which has been coated with the emollient, can be held to a less harmful level, as is achievable when using conventional emollients.

However, because the coating of the lipophilic emollient, produced on skin by a composition in accordance with the present invention, absorbs less UV than would a conventional non-volatile emollient, the overall amount of radiation required in order to achieve a therapeutic effect is reduced. By virtue of their spreading properties, compositions of the present invention leave a thin and highly uniform layer of the lipophilic emollient on the skin, in contrast to the more viscous or more polar conventional emollient compositions which are difficult to apply in a consistantly uniform thickness. The thinness of the layer of emollient left on the skin by a composition in accordance with the present invention allows the amount of UV required to achieve a particular UV dose to the skin to be reduced still further. Although this has little, or no effect on the UV dose received by areas coated in emollient (because the dose of incident radiation is reduced in compensation for reduced absorption by the emollient), areas of skin which have been accidentally left uncoated and areas which cannot be coated, such as the eyes and lips, will receive a lower dose of ultraviolet radiation. As a result, the overall risk of causing cancer, ocular side effects and painful erythema is reduced by using a composition in accordance with the present invention. Thus, contrary to initial expectations, an emollient which absorbs very little UV is safer in use than one whose absorption is significant. Also, being non-viscous, a composition in accordance with the present invention flows readily and, thus, is easy to apply without leaving gaps of uncoated skin. However, because the lipophilic emollient is non-volatile, it remains present on the skin for long enough for treatment to be completed.

Preferably, after application to healthy normal skin, the emollient transmits through to the skin 90% or more and, more preferably, 95% or more incident UVA, UVB or broad band UV.

The preferred incident therapeutic radiation is within the UVA region of the electromagnetic spectrum, and the method of treatment is preferably a PUVA treatment.

In a preferred embodiment of the first aspect of the invention the composition has a viscosity of between 5 and 20,000 centipoise and, preferably, a viscosity of between 5 and 2,500 centipoise. Preferably, the lipophilic emollient has a partial vapour pressure of 17.5 mmHg, or less, and, preferably, 10 mmHg, or less, at 20° C. Also, it is preferred that the partial vapour pressure of a coating, formed by the composition on skin or a like surface, should be 17.5 mmHg, or less, and preferably, 10 mmHg, or less, at 20° C. for a period of sufficient length for a therapeutically effective dose of incident radiation to be administered.

In a preferred form, an inventive composition of either aspect comprises a carrier for the lipophilic emollient. The carrier has the property of enhancing the spreadability of the composition and, therefore, assists the lipophilic emollient to spread evenly into a thinner and/or more uniform coating on skin. This property allows thick or solid lipophilic emollients to be employed. Also, the preferred carriers can cause the composition to creep across a surface and, thus, assist in the formation of an even and unbroken coating of the lipophilic emollient. Preferably, the carrier comprises a substantially non-polar solvent. Non-polar solvents, useful in the practice of this invention, will not form beads when spread on skin or a like surface. Suitable solvents include cyclomethicone, octamethylcyclo- tetrasiloxane (ABIL K4, available from Goldschmidt GmbH of Essen, Germany), decamethylcyclopentasiloxane (ABIL B8839, available from Goldschmidt GmbH of Essen, Germany), a dimethicone, or a mixture of any of these and, preferably, is cyclomethicone. In embodiments where a carrier, including a non-polar solvent, is employed, the coating of lipophilic emollient formed on application to skin can include a proportion of the non-polar solvent. However, a significant proportion of the non-polar solvent will have evaporated or have been otherwise lost from the composition, by the time it has spread to leave a uniform coating of lipophilic emollient.

In further embodiments the carrier comprises a surfactant, which can be isopropylisostearate, pentaerythratol tetraisostearate, promyristyl propionate, myristyl lactate, oleyl erucate, isopropyl myristate, isocetyl stearate, or a mixture of any of these and, preferably, is isopropylisostearate. The surfactant can be used together with a non-polar solvent, to form the carrier. When a surfactant is used, it can also remain present, to a greater or lesser extent, in the coating of lipophilic emollient formed after the composition has spread out on a surface.

The lipophilic emollient, preferably, is coconut oil, sesame oil, sunflower oil, corn oil, a mineral oil such as liquid paraffin or a fraction thereof, any other like saturated oil or, a mixture of any of these, and more preferably, is coconut oil.

In a preferred embodiment the composition is formulated to be suitable for spray application. When so formulated the composition can be sprayed on to the skin to rapidly coat the latter with a substantially uniform film of the emollient. The emollient can be a modified coconut oil.

In a further aspect of the present invention there is provided a spray applicator, filled with a composition in accordance with the present invention. Advantageously, such an applicator provides a highly convenient means of applying the composition, prior to treatment with ultraviolet light.

The dermatological disorders to which the present invention is applicable include those which result in scaley formations in the stratum corneum. The most preferred disorder is psoriasis.

In preferred forms of the inventive composition, which include a surfactant, the latter increases the spreadability of the lipophilic emollient and assists the emollient's penetration of the stratum corneum. When a non-polar solvent is used, it reduces the oiliness and viscosity of the composition, so that a uniform and thin film of emollient remains on the skin after application. In such an embodiment the preferred emollient is coconut oil. Natural coconut oil melts at around room temperature and, thus, is difficult to apply to the body. When formulated in the aformentioned manner, the oil may be sprayed on without difficulty. Most preferably, the composition comprises coconut oil, Isopropylisostearate and cyclomethicone.

Examples of emollient compositions in accordance with the present invention are set out in Examples 1 and 2.

EXAMPLE 1

Composition A 100 grams of natural coconut oil is blended with 100 grams of Isopropylisostearate and 100 grams of cyclomethicone, to provide a non-viscous liquid composition. The liquid is packaged in equal 50 gram portions in six 100 ml capacity pump action spray cannisters.

EXAMPLE 2

Composition B

A non-viscous liquid composition was made up from the same constituents and in the same quantities as described in Example 1. To this composition, 15 grams of 8-methoxypsoralen was added and dissolved therein. The resulting solution was packaged in pump action spray cannisters, in the manner described in Example 1.

Examples of the use of Compositions A and B are set out below. Further compositions can be made up from combinations of the non-polar solvents, surfactants and lipophilic emollients listed in the foregoing description, using the method set out in Example 1.

These further compositions, optionally, include a psoralen or other melanin stimulant and some do not include a surfactant or a non-polar solvent, while others include a plurality of at least one of these components.

EXAMPLE 3

Prior to treatment with UVA a patient suffering from psoriasis should receive a therapeutically effective dose of trimethylpsoralen or 8-methoxypsoralen. If the latter is used, it may be administered orally, at a dose of about 0.6 mg/Kg body weight. After two hours and immediately before treatment, a patient's body should be sprayed with a uniform layer of composition A. The composition is easily applied and tends to spread to cover any gaps or areas of light application.

Once coated in emollient, the patient undergoes UVA treatment for between 2 and 5 minutes in a conventional UVA light cabinet, after which the emollient may be washed off. Treatment normally involves 2–3 such exposures for 4–8 weeks, until the diseased areas have reverted substantially back to normal. Thereafter, the disease may be held in check by a maintenance regime of 1PUVA treatment per week over an indefinite period.

EXAMPLE 4

Use of Composition B

A patient suffering from extensive psoriasis should be sprayed over his entire body with a uniform layer of composition B. As with composition A, composition B is easily applied and tends to spread to cover any gaps or areas of light application. However, unlike when using composition A, it is not necessary for a separate dose of a psoralens to be given and, accordingly, the patient may enter the UVA light cabinet shortly after being sprayed with composition B. It may be necessary for the patient to wait a while before entering the light cabinet, in order to allow sufficient of the 8-methoxypsoralen to be absorbed into the epidermis. The treatment regime is the same as set out in Example 3, i.e. 2–3 exposures to UVA per week for 4–8 weeks, followed by a maintenance regime of 1 PUVA treatment per week.

Whole body light cabinets which are suitable for use in the manner set out in either Example 3 or 4 are listed in P. J. Mounford, "Phototherapy and PhotoChemotherapy Ultraviolet Irradiation Equipment", Photodermatology 1986:3:83/91. The exact exposure times for each particular light cabinets should be determined by a responsible clinician in the normal manner.

I claim:

1. An emollient composition for use in a psoriasis treatment in which abnormal skin is exposed to incident therapeutic radiation, comprising a lipophilic emollient and an active agent, wherein said active agent is trimethylpsoralen, 8-methoxypsoralen or urocanic acid, said lipophilic emollient spread in a 5 μm thick layer absorbs 20% or less of the incident therapeutic radiation, the composition is a non-viscous liquid which, on application to skin, spreads to provide a substantially uniform coating of the lipophilic emollient and active agent, and the coating does not absorb a significant amount of the incident therapeutic radiation and is sufficiently non-volatile to persist for a period of sufficient length, for a therapeutically effective dose of incident radiation to be administered.

2. An emollient composition as claimed in claim 1, wherein a 5 μm layer of the lipophilic emollient absorbs 20% or less incident radiation at any wavelength within the broad band UV, UVA or UVB regions of the electromagnetic spectrum.

3. An emollient composition for use in a psoriasis treatment in which abnormal skin is exposed to incident therapeutic radiation, comprising a lipophilic emollient and an active agent, wherein the active agent is trimethylpsoralen, 8-methoxypsoralen or urocanic acid, the composition is a liquid having a viscosity of between 5 and 20,000 centipoise which, on application to skin, spreads to provide a substantially uniform coating of the lipophilic emollient and active agent, and the coating does not absorb a significant amount of the incident therapeutic radiation and is sufficiently non-volatile to persist for a period of sufficient length, for a therapeutically effective does of incident radiation to be administered.

4. An emollient composition for use in a psoriasis treatment in which abnormal skin is exposed to incident therapeutic radiation, comprising a lipophilic emollient and an active agent, wherein the active agent is trimethylpsoralen, 8-methoxypsoralen or urocanic acid, the lipophilic emollient has a partial vapor pressure of 17.5 mmHg, or less, at 20° C., the composition is a non-viscous liquid which, on application to skin, spreads to provide a substantially uniform coating of the lipophilic emollient and active agent ,and the coating does not absorb greater than 20% of the incident therapeutic radiation and is sufficiently non-volatile to persist for a period of sufficient length, for a therapeutically effective dose of incident radiation to be administered.

5. An emollient composition as claimed in any of claim 1, wherein the partial vapour pressure of a coating, formed by the composition on skin is 10 mmHg, or less, at 20° C., for a period of sufficient length for a therapeutically effective dose of incident radiation to be administered.

6. An emollient composition as claimed in any one of claims 1–4, wherein the incident therapeutic radiation is of a wavelength within the broad band UV, UVA, or UVB regions of the electromagnetic spectrum.

7. An emollient composition, as claimed in any of claims 1–4, further comprising a carrier for the lipophilic emollient.

8. An emollient composition as claimed in claim 7, wherein the carrier comprises a substantially apolar solvent.

9. An emollient composition, as claimed in claim 8, wherein the apolar solvent is cyclomethicone, octamethylcyclotetrasiloxane, decamethylcyclopentasiloxane, a dimethicone, or a mixture of any of these.

10. An emollient composition, as claimed in claims 7, wherein the carrier comprises a surfactant.

11. An emollient composition as claimed in claim 10, wherein the surfactant is isopropylisostearate, pentaerythratol tetraisostearate, promyristyl propionate, myristyl lactate, oleyl erucate, isopropyl myristate, isocetyl stearate, or a mixture of any of these.

12. An emollient composition, as claimed in any one of claims 1–4, wherein the lipophilic emollient is coconut oil, sesame oil, sunflower oil, corn oil, a mineral oil, liquid paraffin, saturated oil, a fraction of any of these, or, a mixture of any of these.

13. An emollient composition, as claimed in any of claims 1–4, wherein said trimethylpsoralen, or 8-methoxypsoralen is present in a concentration of between 0.1 and 10% by weight.

14. An emollient composition, as claimed any one of claims 1–4, wherein the incident therapeutic radiation is within the UVA region of the electromagnetic spectrum.

15. A spray applicator filled with a composition, as claimed in any one of claims 1–4.

16. An emollient composition, as claimed in any one of claims 1–4, wherein said trimethylpsoralen, or 8-methoxypsoralen is present in a concentration of between 0.1 and 10% by weight.

17. A composition, for application to the skin of a subject for treating psoriasis, comprising a non-viscous liquid which includes a lipophilic emollient and an active agent, said liquid having a viscosity of 5–20,000 centipoise and being capable of forming a uniform layer of the lipophilic emollient on the skin of said subject with a thickness of approximately 5 μm, said layer being transparent to 80% of a wavelength of therapeutic radiation selected from broad band UV, UVA and UVB, at said thickness, and having a partial pressure less than or equal to 17.5 mm Hg at 20° C., said composition being for application prior to said subject receiving a therapeutically effective dose of incident radiation and said layer remaining on said skin, during the administration of the therapeutically effective dose of incident radiation, to direct radiation to the epidermis, said active agent comprising trimethoxypsoralen, 8-methoxypsoralen or urocanic acid.

18. A composition, for application to the skin of a subject for treating psoriasis, including a lipophilic emollient selected from the group consisting of coconut oil, sesame oil, sunflower oil, corn oil, mineral oil, liquid paraffin, saturated oil, a fraction of any of these, and a mixture of any of these; an active agent selected from the group consisting of trimethylpsoralen, 8-methoxypsoralen and urocanic acid; and a carrier comprising an apolar solvent selected from the group consisting of cyclomethicone, octamethylcyclotetrasiloxane, decamethyl-cyclopentasiloxane, a dimethicone, and a mixture of any of these, and/or a surfactant selected from the group consisting of isopropylisostearate, pentaerythratol tetraisostearate, promyristyl propionate, myristyl lactate, oleyl erucate, iropropyl myristate, isocetyl stearate, and a mixture of any of theses; said composition for application prior to said subject receiving a therapeutically effective dose of incident radiation and being capable of forming a uniform layer on the skin of said subject, which remains on said skin during the administration of the therapeutically effective dose of incident radiation to direction radiation to the epidermis; and said lipophilic emollient being such that, when spread in a 5 μm thick layer, it absorbs 20% or less of the incident therapeutic radiation.

19. An emollient composition for use in treating psoriasis in which abnormal skin is exposed to incident therapeutic radiation, comprising a relatively non-volatile lipophilic emollient and urocanic acid, wherein the composition is a non-viscous liquid which, on application to the skin, spreads to provide a substantially uniform coating of the lipophilic emollient, and wherein the coating does not absorb greater than 20% of the incident therapeutic radiation and is sufficiently non-volatile to persist for a period of sufficient length, for a therapeutically effective dose of radiation to be administered.

20. An emollient composition as claimed in claim 19, wherein the incident radiation is within the broad band UV, UVA or UVB regions of the electromagnetic spectrum.

21. An emollient composition as claimed in claim 19, wherein the incident radiation is between 285 and 400 nm, between 320 and 400 nm or, between 285 and 320 nm.

22. A method of treating psoriasis, comprising applying an emollient composition, as claimed in any of claims 13–14 and 16, at least to skin areas effected by said disorder and irradiating at least said skin areas with therapeutic radiation.

* * * * *